United States Patent [19]

Cluff et al.

[11] 4,014,328
[45] Mar. 29, 1977

[54] BLOOD SAMPLING AND INFUSION CHAMBER

[76] Inventors: Kenneth C. Cluff, 443 N. 600 East, Oren, Utah 84057; Larry L. Bruce, 4029 S. 45th Place, Phoenix, Ariz. 85040

[22] Filed: June 23, 1975

[21] Appl. No.: 589,018

[52] U.S. Cl. .......................... 128/214 R; 128/2 F
[51] Int. Cl.² ........................................ A61M 5/00
[58] Field of Search ............ 128/214 R, 214.2, 2 R, 128/272, 2 F

[56] References Cited

UNITED STATES PATENTS

| 2,886,035 | 5/1959 | Loutz | 128/272 |
|---|---|---|---|
| 3,416,567 | 12/1968 | Von Dardel et al. | 128/214 R X |
| 3,447,570 | 6/1969 | Collins | 128/214 R X |
| 3,613,663 | 10/1971 | Johnson | 128/214 R X |
| 3,898,988 | 8/1975 | Morgan | 128/214 R |

*Primary Examiner*—Dalton L. Truluck
*Attorney, Agent, or Firm*—Warren F. B. Lindsley

[57] ABSTRACT

A blood sampling and infusion chamber including blood entry and exit ports contoured to accept standard cannula tips for connection in series with the flow of blood through a patient's veins or arteries and a self-sealing cover-block which permits repeated access to the blood flowing through the chamber, the access being accomplished by means of a standard hypodermic needle passing through the self-sealing cover-block.

9 Claims, 5 Drawing Figures

U.S. Patent  Mar. 29, 1977  4,014,328
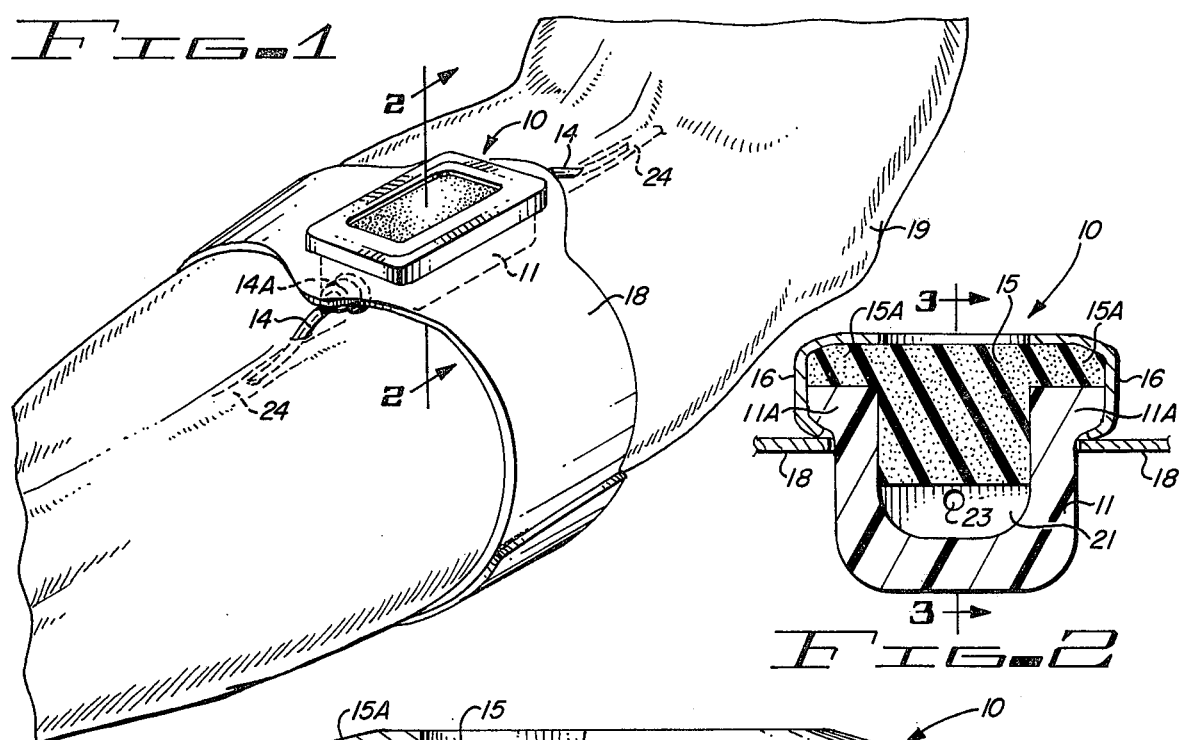
FIG-1
FIG-2
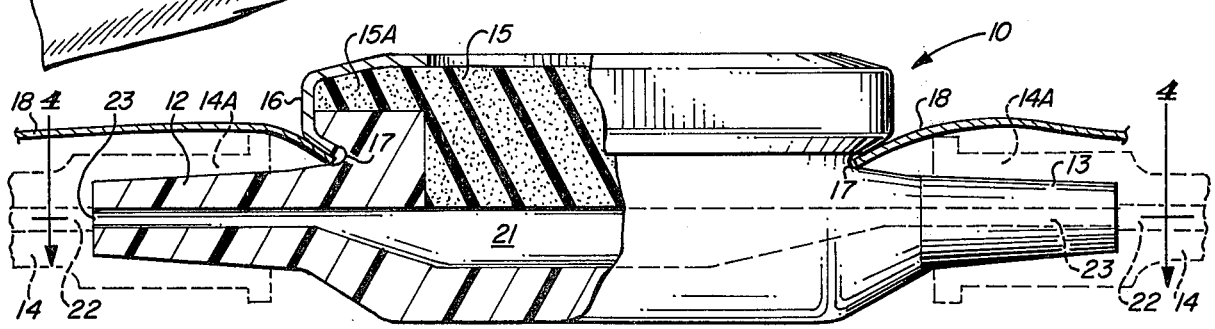
FIG-3
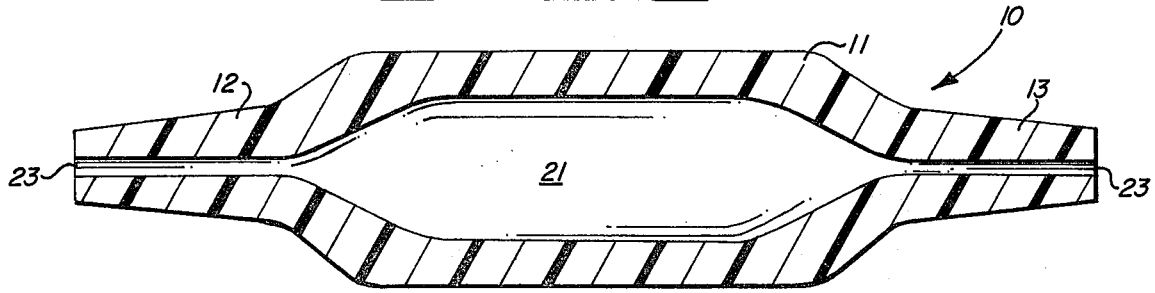
FIG-4
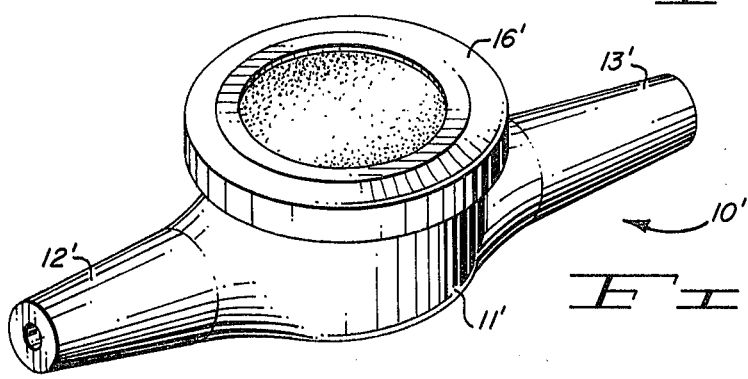
FIG-5

4,014,328

BLOOD SAMPLING AND INFUSION CHAMBER

BACKGROUND OF THE INVENTION

In connection with hospitalizations for various illnesses or conditions, one of the most prominent causes for discomfort or unpleasantness and in some cases, also of injury and possible infection, is the repeated necessity for taking blood samples, for administering intravenous feeding and for injections of various medicines or drugs into the bloodstream by means of a hypodermic needle. For many persons, the veins are relatively prominent and accessible, but in a substantial percentage of patients, especially those who are overweight, the blood vessels are difficult to locate and repeated attempts are required to strike the vein or artery. Furthermore, it is often necessary to repeat such procedures several times a day for days or weeks in succession. Some patients in such circumstances suffer serious consequences such as bruised and swollen arms and inflamed blood vessels which do not recover until weeks after such injury has been sustained. In some cases, the patient suffers severe emotional trauma during and also in anticipation of such procedures, and the trauma can interfere with the patient's recovery from his illness.

There is therefore an important need for improved devices and techniques for such procedures of this nature which will eliminate or significantly reduce the associated discomfort and injury.

SUMMARY OF THE INVENTION

In accordance with the invention claimed, a special device is provided in the form of a small chamber which is connectable in series with a patient's blood stream to provide repeated access thereto over a period of several days, such access allowing the taking of blood samples, intravenous feeding and infusion of medicines or drugs repeatedly without requiring on each occasion the use of a hypodermic needle.

It is, therefore, one object of this invention to provide a special infusion and sampling chamber for connection in a person's bloodstream.

Another object of this invention is to provide such a chamber which is conveniently installable and which can be left in place without causing significant discomfort or unpleasantness to the patient.

A further object of this invention is to provide such a chamber with a self-sealing membrane which will permit the repeated collection of blood samples or the infusion of various solutions and drugs by means of a needle with access to the chamber provided through the membrane and without the necessity each time for penetrating the flesh and blood vessel.

A still further object of this invention is to provide such a chamber which is designed to reduce to a minimum the possibility of cell damage or clotting of the blood which passes through it.

A still further object of this invention is to provide such a chamber along with a convenient means for securing comfortably to the patient's arm or leg.

A still further object of this invention is to provide such a chamber with provision for connection into blood veins or arteries by means of conventional cannula commonly employed for related medical procedures.

A still further object of this invention is to provide such a chamber which may be inexpensively produced from materials which are inert and compatible with the patient's blood and which are compatible with the maintenance of sterile conditions as required to prevent infection.

Further objects and advantages of the invention will become apparent as the following description proceeds and the features of novelty which characterize this invention will be pointed out with particularity in the claims annexed to and forming a part of this specification.

BRIEF DESCRIPTION OF THE DRAWING

The present invention may be more readily described by reference to the accompanying drawing, in which:

FIG. 1 is a perspective view of the blood sampling and infusion chamber of the invention shown attached to a patient's arm and connected to his bloodstream;

FIG. 2 is a cross-sectional view of the chamber of FIG. 1 taken along line 2—2 of FIG. 1;

FIG. 3 is a second cross-sectional view of the chamber of FIGS. 1 and 2 taken along line 3—3 of FIG. 2;

FIG. 4 is a third cross-sectional view of the chamber of FIGS. 1-3 taken along line 4—4 of FIG. 3; and FIG. 5 is a perspective view of a geometric variation of the chamber of FIGS. 1-4.

DESCRIPTION OF THE PREFERRED EMBODIMENT

Referring more particularly to the drawing by characters of reference, FIGS. 1-4 disclose a novel blood sampling and infusion chamber 10 comprising a shallow rectangular box-like housing 11 having hollow tapered entry and exit ports 12 and 13 at opposite ends of the chamber, the ports being appropriately contoured for connection to standard cannula 14 which are inserted into the patient's bloodstream to permit the flow of blood through the chamber, a resilient plug means such as a rectangular cover block 15 which is made of a self-sealing plasticized rubber material and which is dimensioned to fit snugly inside the housing 11 with horizontal perpendicular projection 15A fitting over the top surfaces of the vertical walls of housing 11, and a snap-on retaining cover 16 in the shape of a picture frame, the cover 16 serving to hold the cover block 15 in place inside housing 11 to prevent the loss of blood or other fluids from chamber 10.

The housing 11 has the general shape of a very shallow miniature shoe box but with proportionally substantially thicker side and bottom panels and with horizontal outwardly flared edges 11A surrounding the top edges of its vertical walls, the edges 11A serving as a projection which is gripped by the inwardly extending, wrap around edges of retaining cover 16.

A flexible band 18 having a rectangular opening, the edges of which fit inside a groove 17 formed in housing 11 resembles a plastic or fabric watch band and is used for convenience in fastening housing 11 to the arm 19 or leg of the patient as shown in FIG. 1. Its overlapping ends which are obscured in FIG. 1 by the arm of the patient, may have its mating surfaces coated with a gripping material similar to the known "Velcro" band material.

It should be noted that band 18 fits over the top of the cannulas 14 at the point of connection with the infusion chamber 11 in order to protect them against accidental removal from the chamber. Further, this arrangement of the band to the infusion chamber not only securely holds the chamber in place but permits more pressure to be applied to the chamber to cause compression to be applied to the blood vessel. It is believed that this slight compression will be desirable to insure proper circulation of the blood around and through the chamber. A convex exterior bottom to the chamber would also aid in accomplishing the desired compression on the blood vessels by the cannulas.

The entry and exit ports 12 and 13 are shaped appropriately to accept a standard cannula tip termination 14A commonly known as a Luralock tip.

Appropriate materials for the fabrication of the housing 11 and the retaining cover 16 include high density polyurethane and polyethelene. Both this material and the plasticized rubber material from which the cover block 15 is fabricated, are heperonized (impregnated with a special chemical) to prevent clotting of the blood as it passes through.

The interior of housing 11 together with the lower surface of cover block 15 form a chamber 21 through which the blood passes at a reduced flow rate by virtue of the enlarged cross-sectional area of chamber 21 relative to the cross-section of the blood vessels and of openings 22 in cannula 14 and openings 23 in ports 12 and 13. The reduced flow rate reduces the damage to blood cells as they pass through the chamber 10.

To install chamber 10, the cannulas 14 are first inserted into the veins or arteries by known standard means which entails the use of a hollow stainless steel needle which fits inside the opening 22 of the cannula during the installation procedure, the steel needle serving to pierce the flesh and the blood vessel and to mechanically reinforce the otherwise soft and flexible cannula walls. Once the insertion is completed, the needle is withdrawn. When both of the cannula 14 have been installed in this manner at appropriately spaced locations on the arm or leg of the patient, chamber 10 is secured in place by means of band 18 and the tips 14A are slipped over the ends of the ports 12 and 13, allowing time after the connection of the first tip and prior to the connection of the second tip for chamber 21 to fill with blood and thereby eliminate the air. If desirable, chamber 21 can be filled with a neutral solution, such as an 0.9 percent saline solution for aiding in the elimination of air in the infusion chamber 10.

Once chamber 10 has thus been installed assuming, of course, that the usual sterile procedures have been followed, it may be left in place and utilized for taking blood samples or for infusion of nutritional or medicinal materials as the need arises without causing additional discomfort or distress to the patient. In all such operations, access is made to the blood supply by means of a hollow needle which enters chamber 21 through cover block 15, its spongy plasticized rubber material forming a seal around the needle and sealing itself off as the needle is withdrawn.

Removal can be easily accomplished by simply removing the band and pulling the chamber, with cannulas attached, straight out of the blood vessel. Compression can then be applied over the vessels.

While the foregoing description has described a chamber 10 of a particular geometric configuration, other configurations can be equally appropriate and are contemplated by this invention, as for example, the circular chamber 10' and housing 11' of FIG. 5 with its circular retaining cover 16' and its entry and exit ports 12' and 13'.

In accordance with the objects of this invention, a novel blood sampling and infusion chamber has thus been provided which effectively eliminates the discomfort and unpleasantness associated with repeated procedures of this nature while fabricating the procedures themselves from the standpoint of the nurse or technician involved. The likelihood of injury or infection as otherwise introduced by repeated insertions of a hypodermic needle is also materially reduced. These objects are achieved in an inexpensive and compact device which is comfortably and conveniently attachable to a patient's arm or leg and connectable to his blood system by means of standard cannula and associated tips. Connections may be made to veins or arteries as desired and the device is thus appropriate for use also in kidney dialysis.

Variations of the cover block to allow direct passage of blood through an external device such as a kidney dialysis machine is possible. This direct passage cover block would not allow intermixing of the processed blood with the unprocessed blood.

Although but two embodiments of the present invention have been illustrated and described, it will be apparent to those skilled in the art that various changes and modifications may be made therein without departing from the spirit of the invention or from the scope of the appended claims.

What is claimed is:
1. Apparatus for blood sampling and infusion comprising:
 a chamber formed from a fluid impervious material having an opening surrounded with an outwardly flared edge, an entry port and an exit port,
 said ports each being contoured for connection to a cannula for insertion into a patient's bloodstream to permit the flow of blood through said chamber,
 a resilient plug means for snugly fitting into said opening and extending part way into said chamber to define a given cavity in said chamber,
 said plug means being provided with a flange extending laterally of its length for seating on said edge of the opening of said chamber,
 said resilient plug means being formed of a nontoxic sterilizable material pierceable by a needle and self-sealing upon withdrawal of the needle to afford removable communication with said cavity by means of a hollow needle supplying or withdrawing fluids between said cavity and a patient,
 a cover for said opening of said chamber,
 said cover extending over the part of said plug means extending outwardly of said opening and overlapping the edges of said plug means seated on said flared edges of said opening in said chamber and fastened to the outside of said chamber,
 and clamping means for engaging the outside of the chamber for fastening the apparatus to the patient,
 the outer periphery of said chamber being provided with a groove within which said clamping means extends in a snug fitting arrangement for firmly holding said chamber to a patient.
2. The apparatus set forth in claim 1 wherein:
 said resilient plug means is impregnated with an anti-blood clotting material.
3. The apparatus set forth in claim 1 wherein:
 said chamber and said resilient plug means are impregnated with an anti-blood clotting material.
4. The apparatus set forth in claim 1 wherein:
 said resilient plug means comprises a plasticized rubber material.
5. The apparatus set forth in claim 1 wherein:

the edges of said cover means snaps over and clasps the underside of said flared edges of said opening.

6. The apparatus set forth in claim 1 wherein:
said chamber is provided with a top and a bottom,
the flared edges of said opening of said chamber being substantially parallel with the outside surface of said bottom of said chamber.

7. The apparatus set forth in claim 1 wherein:
said opening in said chamber is of an elongated configuration, and
said entry and exit ports in said chamber are at opposite ends of said elongated chamber.

8. The apparatus set forth in claim 1 wherein:
said clamping means when fitted into said groove lies over said ports so as to cover cannulas inserted in said ports.

9. The apparatus set forth in claim 8 wherein:
said clamping means covers and applies pressure to cannulas inserted in said ports.

* * * * *